United States Patent [19]

Yost et al.

[11] Patent Number: 5,393,980
[45] Date of Patent: Feb. 28, 1995

[54] QUALITY MONITOR AND MONITORING TECHNIQUE EMPLOYING OPTICALLY STIMULATED ELECTRON EMMISSION

[75] Inventors: William T. Yost, Newport News; Christopher S. Welch, Gloucester; Edmond J. Joe, Newport News; Bill B. Hefner, Jr., Hampton, all of Va.

[73] Assignee: The United States of America as represented by the Administrator of the National Aeronautics and Space Administration, Washington, D.C.

[21] Appl. No.: 60,617

[22] Filed: May 11, 1993

[51] Int. Cl.$^6$ ............................................. G01N 23/227
[52] U.S. Cl. ..................................... 250/306; 250/305; 250/307; 250/310
[58] Field of Search ................. 250/305, 306, 307, 310

[56] References Cited

U.S. PATENT DOCUMENTS

| | | | |
|---|---|---|---|
| 4,590,376 | 5/1986 | Smith | 250/310 |
| 4,945,239 | 7/1990 | Wist et al. | 250/358.1 |
| 5,028,778 | 7/1991 | Ninomiya et al. | 250/306 |
| 5,097,126 | 3/1992 | Krivanek | 250/305 |
| 5,185,524 | 2/1993 | Page | 250/305 |
| 5,260,584 | 11/1993 | Popson et al. | 250/571 |
| 5,289,004 | 2/1994 | Okada et al. | 250/306 |

OTHER PUBLICATIONS

C. S. Welch et al., "OSEE Inspection of Solid Rocket Motor Steel", NASA Conference Publication 3139, Third Conference on NDE for Aerospace Requirements, Proceedings sponsored by NASA George C. Marshall Space Flight Center and the University of Alabama, Huntsville, Ala., Jun. 1991, 40 pages.

Primary Examiner—Jack I. Berman
Assistant Examiner—James Beyer
Attorney, Agent, or Firm—Kimberly A. Chasteen; Harry Lupuloff

[57] ABSTRACT

A light source directs ultraviolet light onto a test surface and a detector detects a current of photoelectrons generated by the light. The detector includes a collector which is positively biased with respect to the test surface. Quality is indicated based on the photoelectron current. The collector is then negatively biased to replace charges removed by the measurement of a nonconducting substrate to permit subsequent measurements. Also, the intensity of the ultraviolet light at a particular wavelength is monitored and the voltage of the light source varied to maintain the light a constant desired intensity. The light source is also cooled via a gas circulation system. If the test surface is an insulator, the surface is bombarded with ultraviolet light in the presence of an electron field to remove the majority of negative charges from the surface. The test surface is then exposed to an ion field until it possesses no net charge. The technique described above is then performed to assess quality.

13 Claims, 9 Drawing Sheets

(OUTPUT VOLTAGE OF PHOTOSENSITIVE DETECTOR)

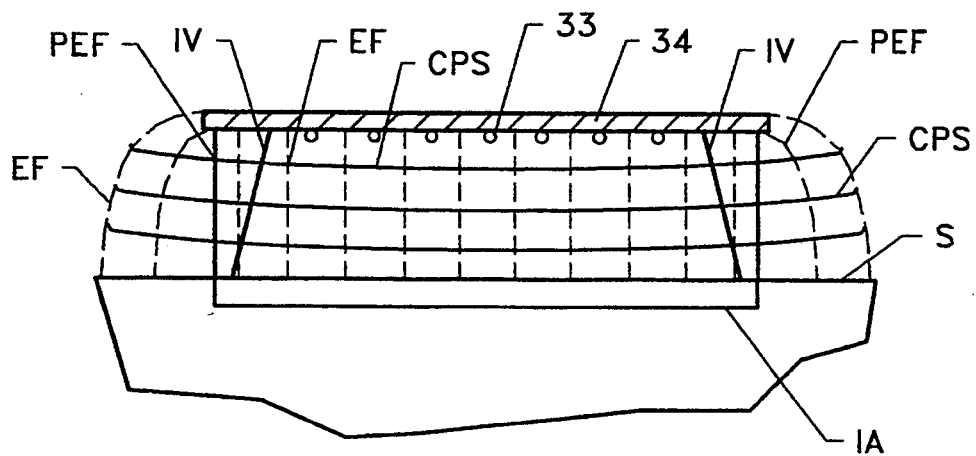
FIG. 10(a)
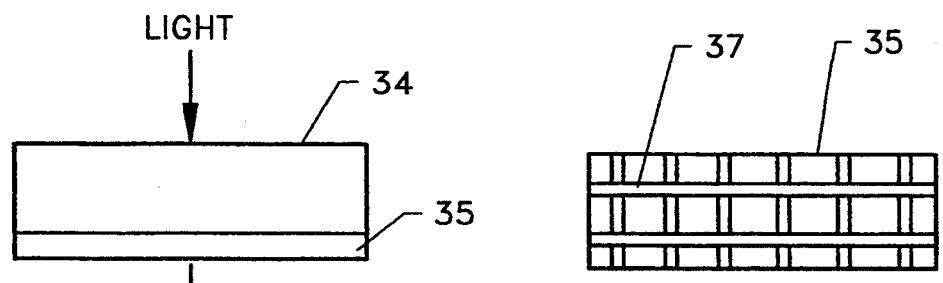
FIG. 10(b)
FIG. 10(c)
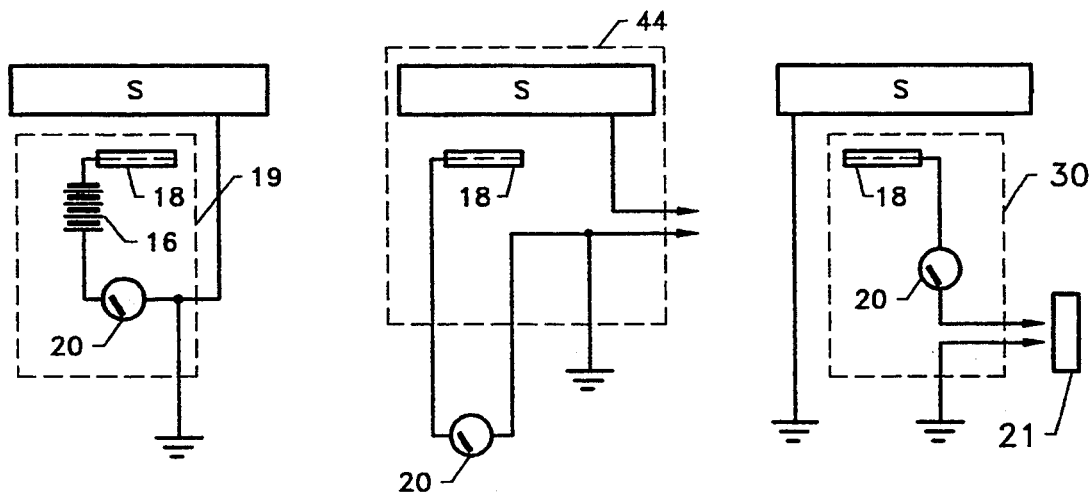
FIG. 13(a)   FIG. 13(b)   FIG. 13(c)
(PRIOR ART)

QUALITY MONITOR AND MONITORING TECHNIQUE EMPLOYING OPTICALLY STIMULATED ELECTRON EMMISSION

ORIGIN OF THE INVENTION

The invention described herein was jointly made by an employee of the United States Government and NASA contract employees during the performance of work under NASA Contract Nos. NAS1-18347 and NAS1-19236, and is subject to the provisions of Public Law 96-517 (35 USC 202) in which the contractors have elected not to retain title.

BACKGROUND OF THE INVENTION

1. Technical Field

The present invention relates generally to the nondestructive evaluation of surface contamination levels and more particularly to improvements to an apparatus and method of monitoring optically stimulated electron emission.

2. Discussion of the Related Art

It is often desirable to monitor the quality and conditions of a surface for various manufacturing processes. For example, the indication, identification and quantification of contaminants such as grease or dirt are vital in painting or coating processes, forming laminates, inspection for cyclic loading, maintaining the cleanliness of memory disc drive heads, etc. One area of particular interest is the placement of coatings or oxides having critical thicknesses onto the surfaces of semiconductor wafers to fabricate microelectronic components.

Several techniques are available to quantitatively observe and to quantitatively measure the condition of a surface and include direct or magnified observation, profilometers, ellipsometry, low energy electron diffraction, Augur electron spectroscopy and scanning electron microscopy. These techniques often require bulky equipment and are difficult for a relatively unskilled technician to operate.

A surface contamination monitor is commercially available from Photo Acoustic Technology, Inc. of Newbury Park, Calif. This surface contamination monitor is described in U.S. Pat. No. 4,590,376 to Tennyson Smith. An ultraviolet light is directed onto the surface of interest, causing photoelectrons to be emitted. These emitted photoelectrons are detected and compared to previously established values for surface conditions to determine acceptability based on criteria such as oxide thickness, contamination or fatigue. This technique is often referred to as Optically Stimulated Electron Emission, or OSEE. The prior OSEE monitor is described in greater detail in the Detailed Description of the present application.

This surface contamination monitor, while offering improved surface monitoring, has several drawbacks. The OSEE indications for a given measurement are time dependent, generally decreasing from an initial high value. For a given sample preparation, there is a large variability of initial values which can be obtained both among samples prepared the same way and from a single sample measured at different times over a period of several days. On a given extended sample measured by scanning, indications of contamination may persist in specific regions, even through several cycles of recleaning. This continued indication of contamination and subsequent good surface performance identify the indications as false positive contamination indications. Finally, oxidation is promoted on some metallic surfaces from exposure to the OSEE probes over extended times. Further drawbacks are discussed in the Detailed Description of the present application.

Objects

It is accordingly an object of the present invention to increase the stability of optically stimulated electron emission measurements.

It is another object of the present invention to increase the reproducibility of optically stimulated electron emission measurements.

It is a further object of the present invention to increase the definition of optically stimulated electron emission measurements.

It is another object of the present invention to increase the sensitivity of optically stimulated electron emission measurements.

It is a further object of the present invention to decrease the ambiguity of optically stimulated electron emission measurements.

It is another object of the present invention to extend the range of substrates measured by optically stimulated electron emission measurements to include non-conductors.

It is a further object of the present invention to accomplish the foregoing objects in an economical, straightforward manner.

Additional objects and advantages of the present invention are apparent from the drawings and specification which follow.

Summary

The foregoing and additional objects are obtained by a quality monitor and quality monitoring technique employing optically stimulated electron emission according to the present invention. A light source directs ultraviolet light onto a test surface and a detector detects a current of photoelectrons generated by the light. The detector includes a collector which is positively biased with respect to the test surface. Quality is indicated based on the photoelectron current. The collector is then negatively biased to replace charges removed by the measurement of a nonconducting substrate to permit subsequent measurements. Also, the intensity of the ultraviolet light at a particular wavelength is monitored and the voltage of the light source varied to maintain the light a constant desired intensity. The light source is also cooled via a gas circulation system. If the test surface is an insulator, the surface is bombarded with ultraviolet light in the presence of an electron field to remove the majority of negative charges from the surface. The test surface is then exposed to an ion field until it possesses no net charge. The technique described above is then performed to assess quality.

BRIEF DESCRIPTION OF THE DRAWINGS

FIG. 10(a) is a side view of a collector grid employing a parallel electric field geometry;

FIG. 10(b) is a side view of a window having a metal coating electrode;

FIG. 10(c) is a bottom view of a metal coating electrode having conductors etched therein;

FIG. 13(a) is a schematic diagram of a prior art circuit having an unvarying bias voltage for the collector; and FIGS. 13(b) and 13(c) are schematic diagrams of circuits for varying the bias voltage of the collector with respect to the test surface according to the present invention.

DETAILED DESCRIPTION

Figure 1:
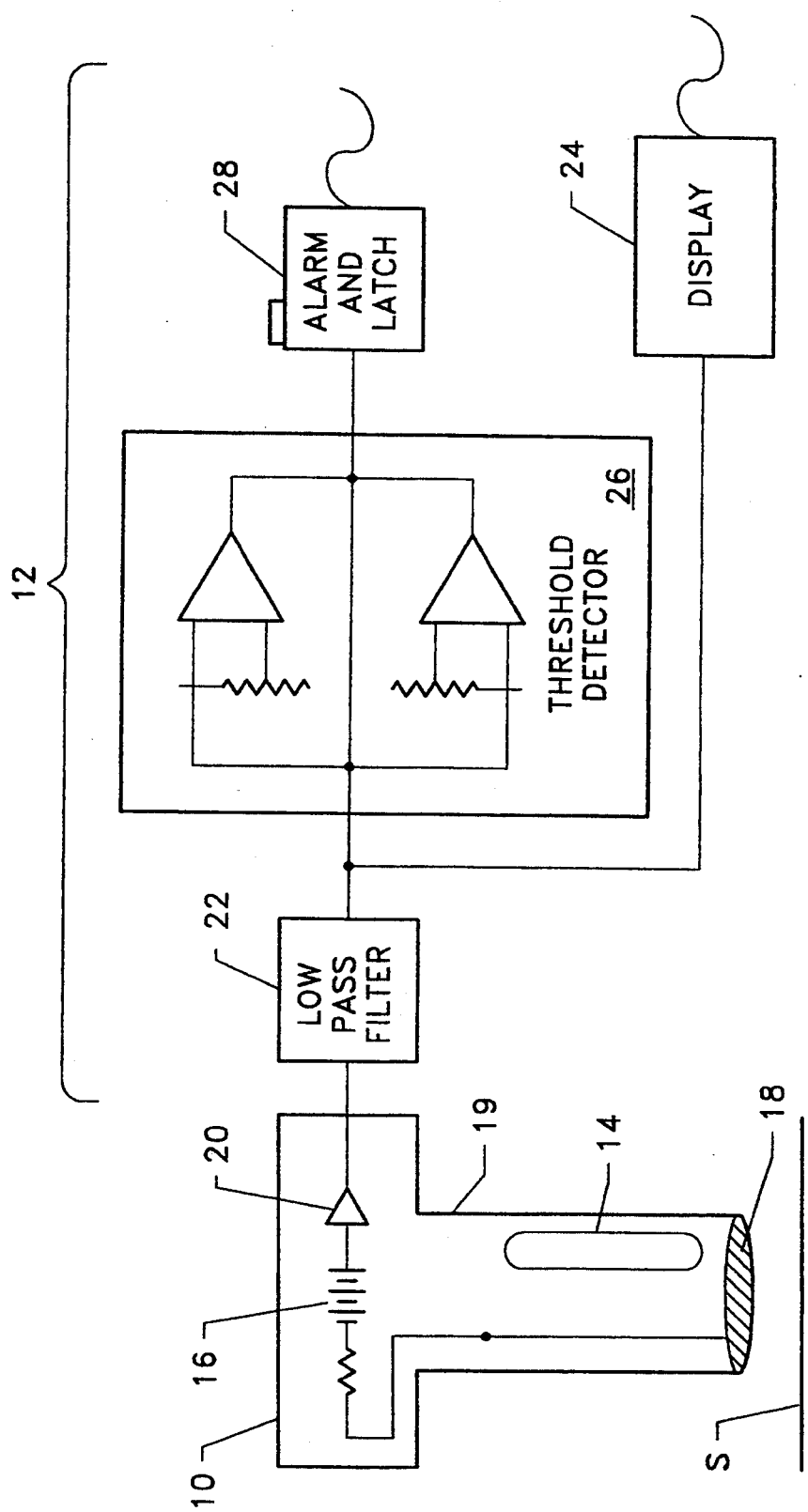
FIG. 1 is a schematic diagram of a prior art monitor for measuring optically stimulated electron emission.

The present invention provides several improvements to the operation of a conventional Optically Stimulated Electron Emission (OSSE) contamination monitor. One such OSEE monitor is commercially available from Photo Acoustic Technology, Inc. of Newbury Park, Calif. and is described more fully in U.S. Pat. No. 4,590,376 to Tennyson Smith, the specification of which is hereby incorporated by reference. FIG. 1 is a schematic drawing of such a prior OSEE monitor. The monitor comprises a sensing unit 10 and a control unit 12. The sensing unit 10 includes an ultraviolet lamp 14, which is usually a low pressure Mercury arc lamp as discussed below, which directs a beam of ultraviolet light onto a surface S of a material to be examined. A battery 16 positively biases a collector 18 made from a metal with a high work function such as a collecting electrode located adjacent the surface S to attract photoelectrons emitted by surface S as a result of the impinging ultraviolet light, as well as to attract negatively charged ions that may be formed by some of the emitted photoelectrons. The resulting photoelectric current of these emitted photoelectrons and negatively charged ions is received by the collector 18, directed through battery 16 and amplified by amplifier 20 to produce a voltage signal proportional to the photoelectric current. An appropriate housing 19 such as a grounded shroud partially surrounds the lamp 14 and collector 18 and includes the battery 16 and amplifier 20. A low pass filter 22 filters the higher frequencies of this signal associated with noise and transmits the signal to display 24 and to a threshold detector 26 which can sound an alarm 28 if a threshold photoelectric current value is exceeded. The photoelectric current is often directly related to many physical properties found at a surface such as oxide thickness, contamination level and mechanical condition. Calibration on surfaces of identical material having a wide variety of values for a particular property are tested to obtain voltages proportional to photoelectric current, whereby calibration curves are generated. Of course, the threshold current value is application specific.

The features of the present invention will now be described. Where applicable, reference will be made to the elements described above in reference to FIG. 1, wherein like numerals shall refer to like elements with like function.

The present invention improves the effectiveness of the conventional OSEE monitor. A five-pronged strategy was implemented to achieve this improvement. The first prong involves increasing the stability of the reproducibility of the OSEE measurement and includes (1) temperature control of the ultraviolet light source lamp, (2) feedback control of the light intensity and (3) use of a purge gas to avoid atmospheric effects, The second prong involves increasing the definition of the OSEE measurement and includes (4) controlling the light spectrum of the ultraviolet source and (5) controlling the distribution of the ultraviolet light. The third prong involves increasing the sensitivity of the measurement and includes previously mentioned item (4) and (6) utilizing a parallel electric field (PEF) geometry for the collector. The fourth prong involves decreasing the ambiguity of the OSEE measurement and includes (7) a concurrent Kelvin probe measurement and (8) operational control of the collector voltage. The fifth prong involves extending the range of substrates measurable by a OSEE monitor to include non-conductors and includes previously mentioned item (8) and (9) replacement or supplementation of the charge collected by the collector.

The radiation from the conventionally unprotected lamp has been found to be highly sensitive to changes in air currents surrounding the lamp and its partial housing 19. It has also been shown to be sensitive to both envelope temperature and to temperature gradients. The air currents may produce temperature changes by altering the cooling efficiency. The changes to the radiation include both amplitude of the individual spectral lines and relative intensities between various lines. With the lamp exposed directly to the environment during scanning, the OSEE values are dependent on drafts, scanning speed, and other factors such as ambient room temperature, humidity, and sample reflectivity which can influence bulb temperature.

Figure 3:
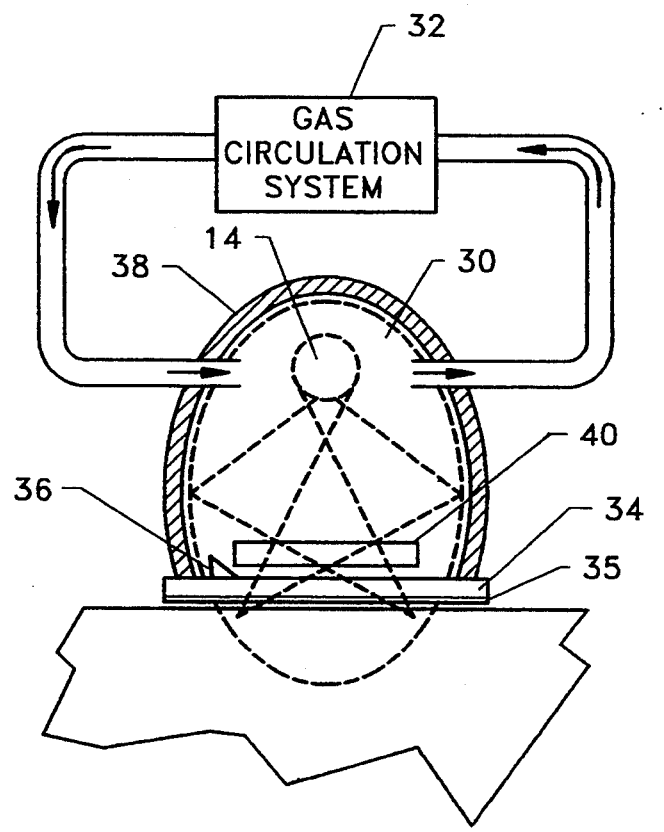
FIG. 3 is a schematic diagram of an OSEE monitor improved according to the present invention.

The improvement here is to control the atmospheric environment of the lamp. Referring to FIG. 3, the lamp 14 is placed in a closed chamber 30 having a window 34 which is transparent to the UV radiation of the light source and is filled with a gas which is also transparent to the UV radiation. The gas is circulated through the chamber via a conventional gas circulation system 32 at a fixed rate to control the cooling. The gas is circulated to promote convection cooling of the lamp to maintain an optimum temperature range, which parameters, produces the maximum OSEE current. The closed chamber with the window thus closes the lamp 14 from direct environmental contact, e.g., it provides an airtight enclosure which is environmentally separate. It is found in manufacturer's specifications and experimental operation that low pressure mercury lamps emit the maxium 185 nm light at a particular envelope temperature, the temperature for an individual lamp depending on the lamp and the location of the temperature probe. Optimum temperatures have been found in the range from 50° C. to 120° C. Operation near the optimum temperature has two advantages. First, it maximizes the amount of light produced for a given voltage input. Second, it minimizes the temperature sensitivity of the amount of light emitted. To operate at this optimum value, the lamp chamber is configured to exclude ambient air and also insulated, so that the primary cooling factor on the lamp is the circulation of the cooling gas. This permits gas flow to be set at a predetermined value which corresponds with the optimum lamp output. As the gas flow is the primary heat load on the lamp, lamp temperature is correspondingly protected from other, uncontrolled factors. As the flow is set to maintain the lamp at optimum temperature, the radiation from the lamp is maximally insensitive to temperature variations. Any suitable gas can be used. Argon was selected for use with a conventional mercury lamp producing line spectrum having wavelengths of 185 nm and 254 nm because of its inert response to light at these wavelengths.

The lamp in the prior art is generally located as close as possible to the measured surface. The OSEE current signal decreases dramatically as the spacing between the electrode 18 and the test surface increases past approximately a quarter of an inch. Three factors have been identified as contributing to this decrease; namely, (1) a decrease in the ultraviolet intensity, (2) a loss of electrons and (3) a weakening of the field due to the limitation of a constant voltage source for the collector electrode as the distance increases from the electrode to the test surface. One result of this is that light strikes a large area of the sampled surface at a variety of intensities. Because the illuminated area extends well beyond the collector, the photoelectrons released encounter a wide variety of electric fields.

Figure 2A:
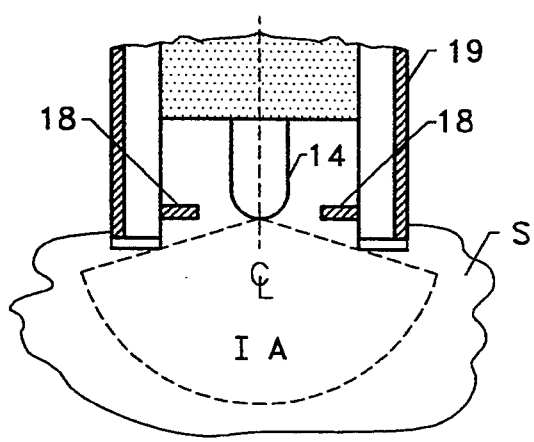
FIGS. 2a and 2b are schematic diagrams of prior art light sources and resulting illuminated areas of the test surface.
Figure 2B:
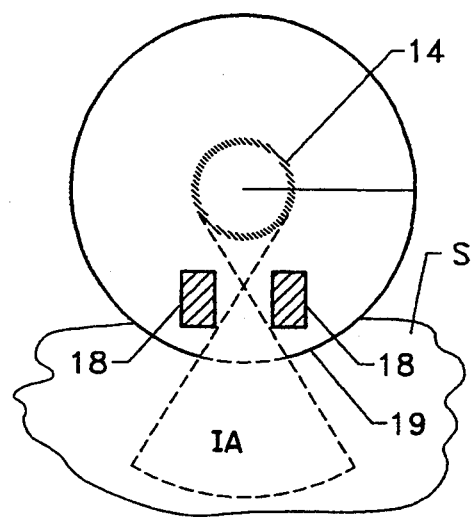

In the presently available commercial instrument, the light presently comes either from the tip of the lamp 14 positioned very close to the inspected surface S or from an extended cylindrical screened lamp 14a positioned parallel to the inspected surface S, as respectively shown in FIGS. 2a and 2b. The light fills an illuminated volume, shown in FIGS. 2a and 2b. The part of the volume cross-section is depicted by a circular ar in these figures is not really defined, as the illumination extends indefinitely along rays of decreasing intensity with distance from the lamp. The rays at the edge of the illuminated volume are called extreme rays, and they correspond to the straight dotted line segments emanating from the lamp nad grazing the limiting aperture. When a sample is brought into a measurement position near the lamp, the portion of the sample within the illuminated volume forms an illuminated area IA on the sample surface, and that area then bounds the illuminated volume. In both cases, the distribution of source positions for OSEE electrons is a complicated function of position of the light source relative the sample surface because both the electric field and illumination intensity are determinants for the resulting electron rate. At the low current densities of, e.g., 100 pico amperes per square centimeter, associated with OSEE measurements, the OSEE currents are generally proportional to the illumination of light at a given wavelength. They are a more complex and nonlinear function of the electric field at the surface. As an example, the distribution of OSEE electrons will vary in a complex manner as the distance from the probe to the sample is varied.

An improvement according to the present invention is to limit the extent of the illuminated area by defining the edge with an aperture and removing the lamp from the sample to increase the numerical aperture of the optical system. This is done by using a suitable reflector for the lamp.

The objective of the improvements is to provide well characterized light to a well-defined region of illumination, in which the electric field at the sample surface is relatively constant. FIG. 3 shows one embodiment incorporating the improvements in the light delivery system. Outside the illuminated volume, the collector electrode is preferably coated with carbon black to absorb as much reflected light as possible. For the distribution of light intensity, a reflector 36 and the aperture 38 are used. The reflector 36 is used to accumulate much of the light from the source, a tube in this case, and direct it in a known manner to the sample surface. In the embodiment shown, the image of the lamp tube is projected onto the sample surface through the use of an ellipsoidal reflector 36 which lines the interior surface of the chamber 30 so that the image of the lamp is centered on one focu of the ellipse. The non-reflected portion of the light is further controlled with an aperture 38, the dotted lines in the figure indicating the spread of the extreme rays which strike the sample surface. Compared with the present practice, as indicated in FIGS. 2a and 2b, this light delivery system has increased intensity and a more clearly defined limit to the illuminated region. Aluminum is a good choice as a reflector for light wavelengths in the vicinity of 200 nm. The distance from 34 and the surface under examination is constant. In one experimental geometry, the lamp is moved about 15 cm from the sample, and an aperture 2.5 cm in diameter is placed about 1 cm from the sample. This produces a numericla aperture of about 0.08. In another geometry, shown in FIG. 3, the center of the lamp is removed to about 1.27 cm from the sample. In this configuration, an ellipsoidal reflector is used to reflect the light rays which would normally be lost because they propagate away from the sample, and two sets of extreme rays are shown corresponding to the direct and reflected light. The curved line denotes only the continuation of the ellipsoidal shape. The light here is controlled by an aperture positioned above the window, and the unit is designed to be operated at a constant distance from the sample.

The light source used in the prior art has been a low pressure mercury arc lamp. Such a lamp emits primarily a line spectrum, two lines of which release photoelectrons in many materials. The OSEE response to contamination is generally different for each of the lines. In order to obtain a pure response which is easily interpreted, a single line selected with a filter is a substantial improvement. In much work, the line at 185 nm is appropriate for OSEE work since it produces the majority of the OSEE current. This can be selected with an optical filter 40 which permits this line to pass and having a passband of several tens of nanometers, as the line to be blocked is at 254 nm. The filter is located between the light source 14 and the test surface S.

The light source for OSEE measurements is of some practical importance. It was found that a low pressure, low power mercury arc lamp, sold as a calibration source for spectrometers, produced higher OSEE currents than a 75 Watt, directed Xenon arc lamp, which required vertical orientation, air cooling, and a bulky power supply. Besides size and ease of use, the major difference between the two lamps was that the arc lamp had a smooth spectrum with a nominal cutoff near 200 nm, while the calibration mercury arc lamp produced a definite line spectrum. Because of the difference in OSSE response, the spectral distribution of the calibration lamp was investigated.

The radiation from low pressure mercury gas discharge lamps occurs primarily as a series of distinct spectral lines. The shortest wavelengths of the spectrum are available to produce OSEE. Waves longer than some cutoff value are not energetic enough to eject electrons from the material. In a low pressure mercury lamp, the radiation between the spectral lines is very low. As the lines are generally well separated and quite narrow, they provide a source from which nearly monochromatic radiation may be selected by means of suitable filters. The shortest wavelength for mercury radiation is at 184.9 nm, and the next ones are at 194.2 nm and 248.2 nm, with some minor ones between. The major ultraviolet mercury line is at 253.7 nm, and the manufacturer of the lamp used, Oriel Corporation, Statford, CT, Model 6035 Spectual Calibration Lamp, asserts that about 90% of the total radiant output is at that line. As wavelength increases, the next lines with even 1% of the intensity of the 253.7 nm line occur at 302.2 nm and 313.2 nm. In another set of measurements, it was found that the line intensities and the ratios of intensities between spectral lines both varied with the voltage setting on an autotransformer used to supply power to the lamp transformer. This variation changes both the current to the lamp and its operating temperature.

The sensitivity of the photoelectric effect to incident light is dependent on wavelength. The photocurrent is produced only by lines with wavelengths shorter than the cutoff. In many cases, the photocurrent reaches a broad maximum for wavelengths about two thirds of the cutoff wavelength. In the vicinity of the cutoff wavelength, the photoyield increases nearly linearly with the difference between the cutoff wavelength and the measured wavelength. Very near the cutoff, a "foot" on this curve can be associated with temperature, the foot having a size of about 1.3 nm at room temperature. Larger "feet" observed on the curve can be caused by unwanted short wave radiation and variations in work function associated with metallurgical variations of the illuminated surface or surface contamination. The implications for OSEE are that photocurrents from radiation with wavelengths longer than 253.7 nm will always be smaller than the current from 253.7 nm radiation. Photocurrents from shorter wave radiation, in particular the 184.9 nm line, will always be larger than the intensity ratio between the lines. If the cutoff wavelength of the clean surface is close to 253.7 nm, the majority of the current can come from the 184.9 nm line, even though its intensity is smaller than the 253.7 nm line. Another consequence of the linear current vs. wavelength characteristic of the photo-yield is that currents from lines close to the cutoff wavelength will undergo larger fractional changes to a change in the surface work function than currents from lines at shorter wavelengths.

Figure 4:
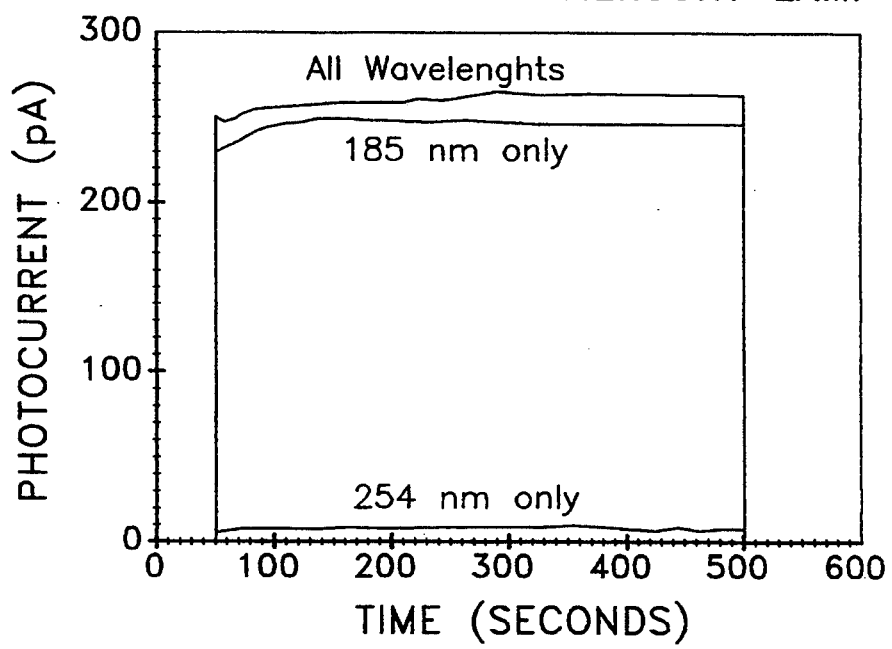
FIG. 4 graphs the OSEE photocurrent responses with respect to various wavelengths of light.

An experimental study was performed using optical filters to determine the relative contributions of the 253.7 nm and 184.9 nm spectral lines to the OSEE response on clean steel. The results for one of the samples examined are shown in FIG. 4. This run shows the OSEE response as a function of time for three sequential measurements of a single clean steel sample. Between the runs, filters were changed in the light path to permit passage of all the light (no filter), only the 184.9 nm line or only the 253.7 nm line. In each case, the filter response is wider than the line width, so the pass value of the filter transmission curve was obtained from its calibration curve and used to compensate for attenuation and express the current as equivalent unattenuated values. The compensation calculation is estimated to have an accuracy of 5%. For all the samples tested, the results showed clearly that more than 95% of the OSEE response for D6AC steel comes from the 184.9 nm line, while less than 5% comes from the 253.7 nm line. As a check, the sum of the amplitudes of the two spectral components was equal to the amplitude of the unfiltered light to within the accuracy of the measurement for all samples tested. Accordingly, an optical filter 40 is selected which filters out the lines of the light source spectrum except that line which produces the maximum photoelectron current from the particular test surface.

Figure 5:
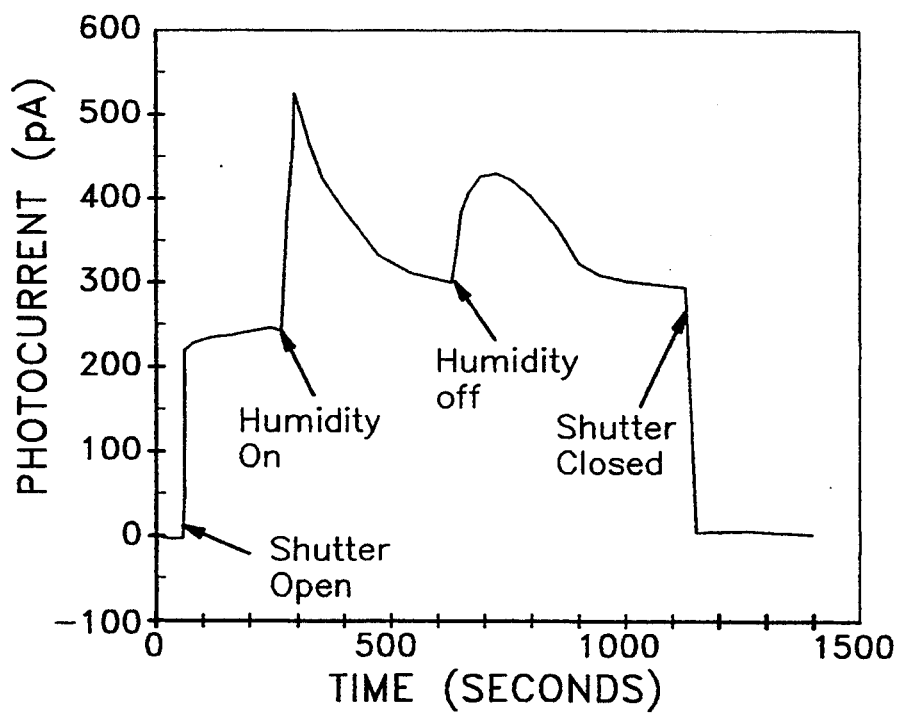
FIG. 5 graphs the OSEE photocurrent response with respect to changing humidity over time.

Experiments have shown the OSEE currents to be highly sensitive to changes in the gaseous environment of the inspected surface. In particular, water vapor, which is a highly variable constituent of the atmosphere, produces changes in OSEE currents. The dramatic effect of water vapor on the OSEE signal as shown in FIG. 5 suggests that humidity is a significant factor influencing day-to-day variability of the OSEE signal. The humidity introduced into the Argon was very high, near the saturation level having a dew point of 70.7° F. The argon environment is nearly dry, so the humidity is controlled by removal, thereby eliminating the confusing effect of humidity. Also, oxygen absorbs the UV radiation to produce ozone, which combines readily with many materials to produce photochemical alterations of the inspected surface. The solution proposed by the present invention is to fill the illuminated area of the surface with a purge gas, such as argon, which is transparent to the UV radiation, does not alter the surface being inspected, and will not participate in photochemistry.

Figure 6:
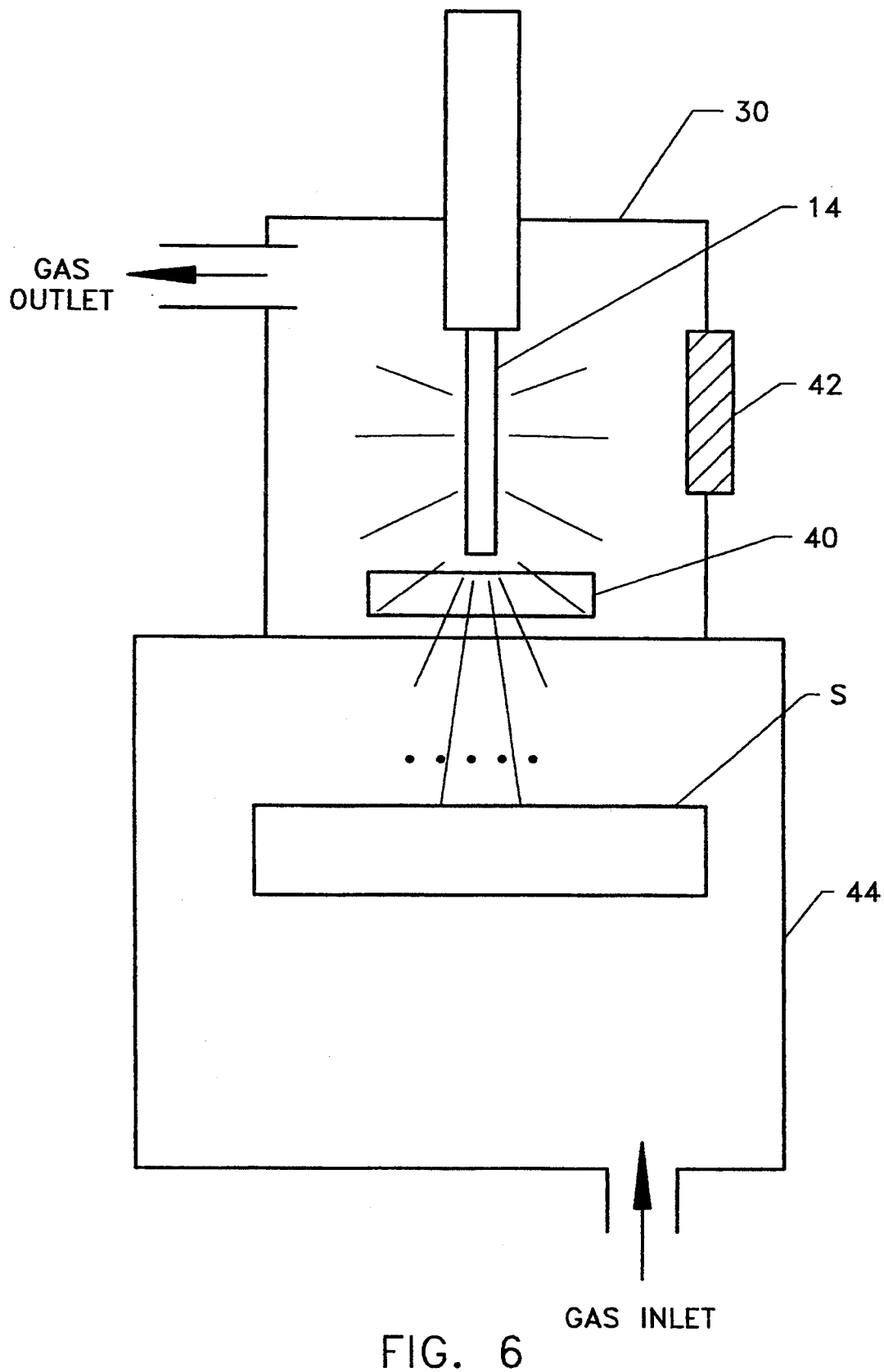
FIG. 6 is a schematic diagram of an embodiment of the present invention employing a purge gas circulation system to compensate for humidity.

Referring to FIG. 6, a purge chamber 44 is provided which surrounds the test sample in an airtight manner and communicates with the chamber 30 surrounding the light source 14 and the filter 40. Note that window 34 of FIG. 3 is removed to facilitate flow of the gas. In the embodiment shown, gas is introduced via a gas inlet into purge chamber 44 surrounding the sample, flowing into chamber 30, and then exits via a gas outlet. The gas inlet and outlet are connected to a conventional gas circulation system as shown in FIG. 3. Accordingly, this embodiment depicted in FIG. 6 accomplishes both the reduction of the effects of the ambient environment on the OSEE process and cooling of the light source. Another embodiment entails providing chamber 44 with a gas outlet and employing a window 34, whereby only environmental protection is achieved. Another embodiment entails separate gas circulation systems for lamp chamber 30 and purge chamber 44, wherein separate gas control and hence additional data stability are obtained.

Figure 7:
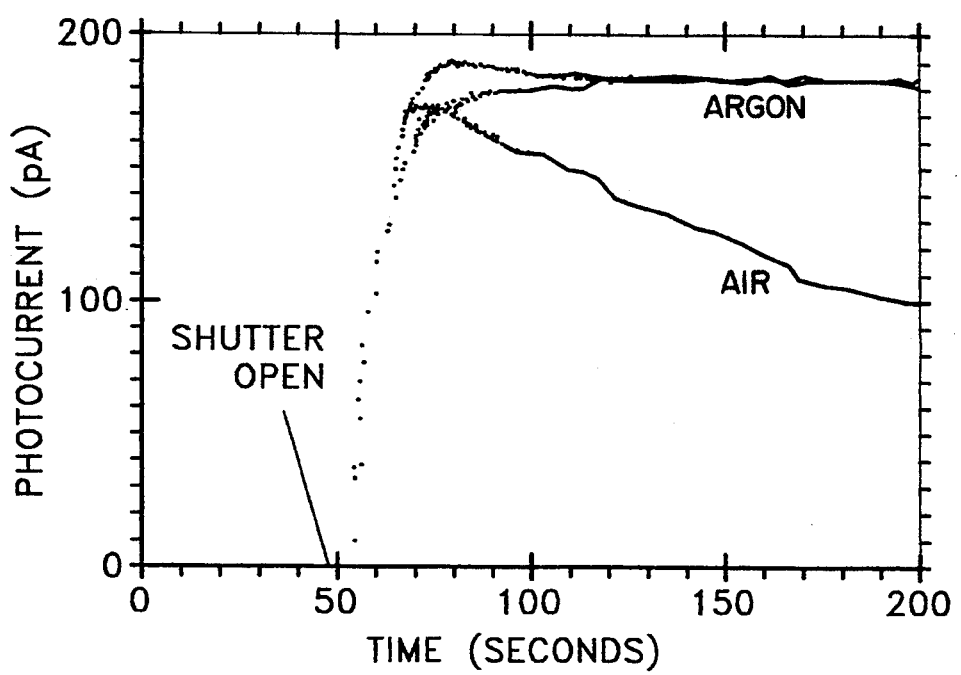
FIG. 7 is a graph showing the effect of ambient air and the effect of Argon purge gas on measured OSEE photocurrent.

FIG. 7 graphs the increased stability of employing an argon atmosphere as compared to an environment containing normal concentrations of water vapor, oxygen and other photochemically activated species. Part of the benefit of the pre-exposure to ultraviolet light in argon may be to remove adsorbed water vapor from the surface under inspection. Pre-exposure means exposure of surface to UV light just prior to taking OSEE current measurement.

Experiments on conducting substrates in which a timed protocol for obtaining OSEE measurements over several minutes duration was repeated several times show a high degree of reproducibility in the second and subsequent repetitions and often some difference in the first repetition. It has become our practice to regard the second and subsequent repetitions as "true" OSEE measurements while the first run is considered a "pre-exposure" run associated with sample preparation rather than part of the measurement. As the repeated measurements were all done in a continuously maintained argon atomosphere, the physical role of the pre-exposure is hypothesized to be the removal of adsorbed water vapor fron the surface under inspection.

Argon has an unusually large conduction for photoelectrons compared to the other constituents of air. The reason may well be its decreasing collision cross-section with energy up to the Ramsauer resonance energy. The effect increases the efficiency of collection of photoelectrons, and by this will increase the signal-to-noise ratio of a given measurement. Such an increase will help inspection operations.

As shown in FIG. 6, photosensitive detector element 42 is used to monitor the radiation at the wavelength of interest, and a control circuit is used to control the lamp voltage based on the photosensitive detector element voltage which is proportional to the sensed intensity of light at a particular wavelength in such a way as to keep the monitored light radiation constant. This feedback control greatly improves the stability of the radiation which produces OSEE currents.

Figure 8:
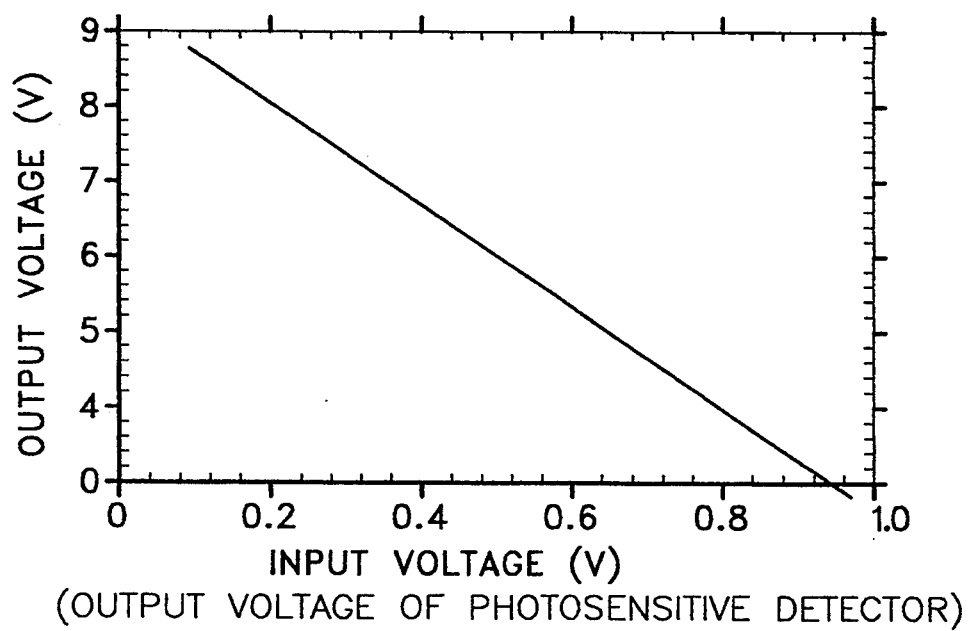
FIG. 8 is a graph of the relationship between output voltage of a control circuit depicted in FIG. 9 for controlling light source voltage and input voltage supplied by a photosensitive detector.
Figure 9:
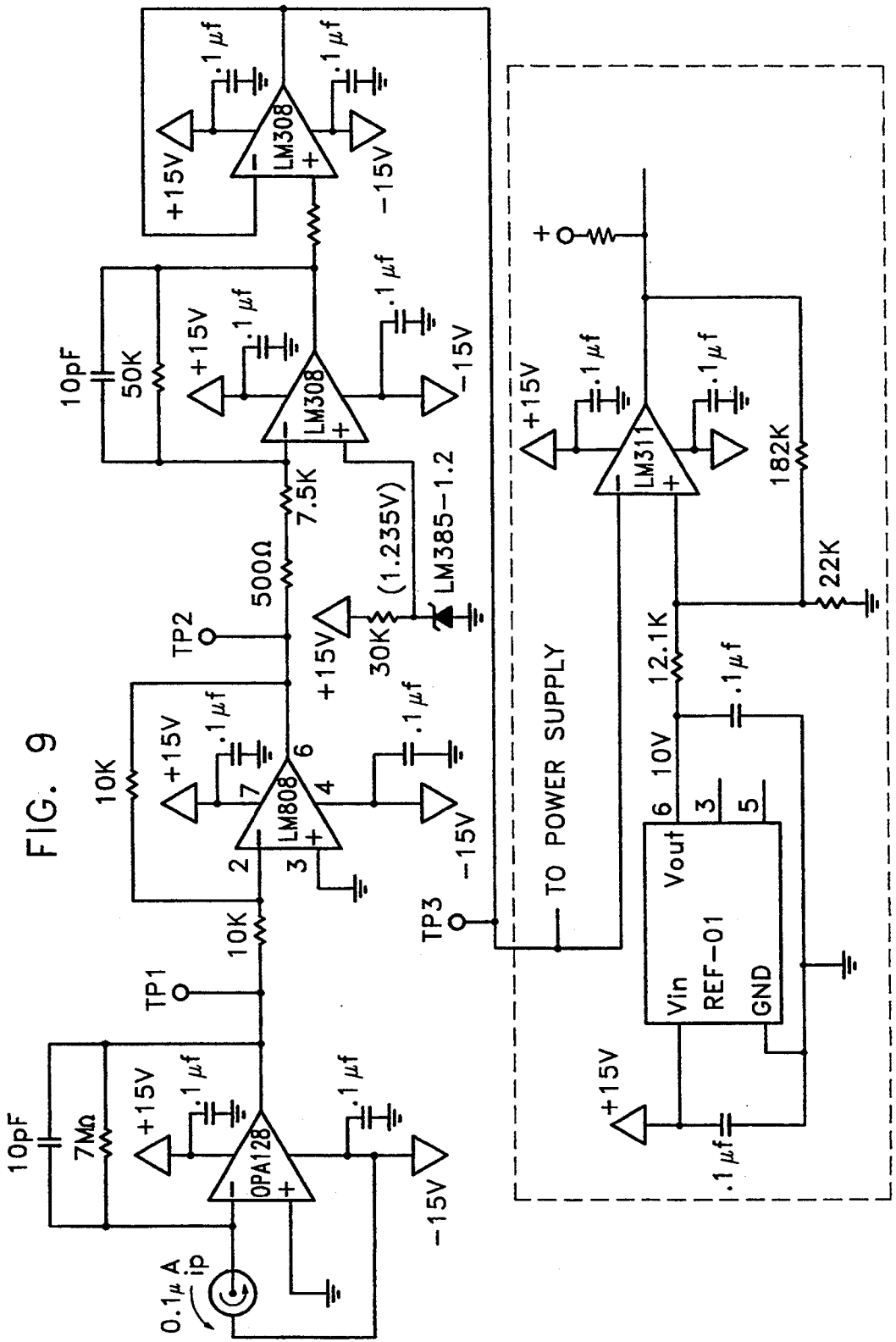
FIG. 9 is a schematic diagram of a control circuit for controlling light source voltage based on detected light wavelength.

FIG. 8 is the graph of the expected output voltage from the feedback circuit shown in FIG. 9 for OSEE. A phototube detects the amount of 185 nm radiation present in the lamp. As the radiation decreases due to the aging of the lamp, the electrical signal from the phototube decreases. This circuit compares a preset nominal value and the actual value. The signal is amplified and is sent to the lamp/power supply. This signal controls lamp power supply by electrically adjusting the amount of current needed to maintain a constant 185 nm radiation intensity on the lamp. An ancillary circuit is added to notify the operator that this voltage has exceeded a preset threshhold and that it is time to replace the lamp. The operating parameters are (1) at minimum input, which is 0.1 V, the output cannot exceed 10 volts and (2) at an input of 0.7 volts, the output must be 4.61 volts.

The formula for the feedback amplifier is $$V_{out} = (-R2/R1)(V1) + (1 + R2/R1)(V2)$$

where

V1=inverted voltage from the detector
V2=voltage from the voltage reference (identify in FIGURE)
R2=feedback resistor, 50 K$\Omega$
R2=input resistor to the inverting input, 8 K$\Omega$.

This circuit is therefore:

$$V_{out} = (-50K/8K)(V1) + (1 + 50K/8K)(1.240)$$
$$V_{out} = -6.25(V1) + 9.00.$$

For an input of 0.7 volts:
solve
$$[\{0.7)(-6.25) + (1.24)(1+6.25) = = x\}, \{x\}]\{\{x \geq 4.615\}\}.$$

For an input of 0.1 volts:
solve
$$[\{(0.1)(-6.25) + (1.240)(1+6.25) = = x\}, \{x\}]\{\{x \geq 8.365\}\}.$$

10% Reduction:

For a decrease of 10% (which is an input of 0.63 volts), the output to the power supply is 5.0525 V (which is an 9.49% increase in current) and this equates to a current of 32.8 mA.

Solve
$$[\{(*0.63)(-6.25) + (1.240)(1+6.25) = = x\}, \{x\}]\{\{x \geq 5.0525\}\}.$$

20% Reduction:

For a decrease of 20% (which is an input of 0.56 volts), the output to the power supply is 5.49 V (which is an 18.96% increase in current) and this equates to a current of 35.7 mA.

Solve
$$[\{(0.56)(-6.25) + (1.240)(1+6.25) = = x\}, \{x\}]\{\{x \geq 5.49\}\}.$$

The OSEE current produced by photoemission is dependent on the strength of the electric field adjacent to the inspected surface. In order that the currents from the entire illuminated region be produced on a common basis, the configuration of the electrode is chosen to provide equipotential surfaces parallel to the inspected surface over the illuminated region. One way of accomplishing this is to form the collector/bias electrode as a grid of wires with the illumination passing through the grid. The resulting field lines are parallel within the inspection volume. In this geometry, the electric field in the illuminated part of the gap was configured to be uniform. Accordingly, the interpretation of the data is not confused by geometrical factors. In the prior art, Smith, in his FIG. 4 illustrates a grid of wires used as a collector. In this example, the grid is simply a convenient way of removing the electrode aperture to approach an inspection geometry having an inside corner. This configuration will not produce, in general, a parallel electric field. The grid is used to produce a parallel electric field which extends well beyond the edge of the illuminated region. It would not be suitable for inspection of inside corners. Another way to produce the parallel electric field is to form the electrode with a very thin layer of metal, such as 1.8 nm of chronium, which is partly transparent to the ultravioleta radiation yet forms an electrically conducting planar surface.

In the OSEE operating environment, the electron transport as follows is described well by the formulas of gaseous conduction at low field-to-pressure ratios and low currents. Physically, that means that no additional ionization is produced through electron collisions with the gas molecules in the gap and that the total charge associated with the charge carriers is small enough that it does not appreciably alter the imposed electric field in the gap, particularly near the sample surface. Under these circumstances, the release of OSEE electrons from a given metallic surface is a nonlinear function of the electric field strength and a strictly linear function of the light intensity. In order to restrict the spatial variability of OSEE production over the illuminated area to match the light intensity variation over the same area, the electric field at the illuminated surface is configured to be constant by utilizing a parallel plate voltage electrode over the sample, which on the scale of the measurement is presumed to be flat.

Referring to FIG. 10(a), a collector electrode 18 is shown to be planar and parallel to the sample, permitting light from the source above to pass through the grid and stride the sample. The collector may be a very thin film 35 of metal such as chrome deposited on the bottom side of the window 34, as shown in FIG. 10(b), a grid of thin parallel conductors 37, etched into such a thin film of metal, as shown in FIG. 10(c), or an array of wires 33 aligned just beneath the glass window. If a grid of conductors or wires is used, the spacing between the electrode and the inspected sample, in order that the field inhomogenieties associated with the discontinuous conductor thus formed be sufficiently reduced at the position of the sample. A region is defined beneath the electrode through which the constant potential surfaces, seen as solid lines CPS in cross-section, are flat and parallel, and through which the electric field lines, seen as dotted lines EF, are also parallel and extend between the grid and sample. This region is called the parallel electric field region and is defined by lines PEF. Parallel electric field geometry is achieved when the illuminated volume IV, defined by lines IR is entirely within the region of parallel electric field.

By producing a uniform electric field within the gap between the electrode and the sample surface, this PEF geometry ensures that a given electron-emitting point will produce the same response regardless of precisely where it is under the sensor.

In comparative measurements shown in Table 1, the measurement sensitivity of the PEF configuration was greater in the contaminant thickness region of greatest interest than that of the commercial equipment.

TABLE 1

| Values | Non-Parallel Surface Geometry Mercury Vapor | Parallel Surface Geometry | | |
| --- | --- | --- | --- | --- |
| | | Mercury Vapor | 185 nm Filtered Out | 254 nm Filtered Out |
| Total | 17.9 | 30.0 | 28.4 | 52.5 |
| Differential | 22.5 | 29.8 | 47.8 | 74.6 |
| Percent Improvement | | | | |
| Total | | 67.6% | 58.7% | 193.3% |
| Differential | | 32.4% | 112.0% | 231.0% |

A characteristic of OSEE which has been well documented by previous investigators is that the signal decreases rapidly as the spacing between the sample and the sensor increases beyond 0.25 inches. This decrease has been attributed to three factors; namely, a decrease of UV intensity, a loss of electrons and a weakening of the field with a constant voltage source and a varying gap. Our results indicate that the decrease in UV intensity is caused by atmospheric absorption of the 184.9 nm mercury line and compounded by the geometrical spreading of the light beam with respect to the electric field distribution. The use of an argon flush with a PEF geometry permits several of these factors to be reduced or eliminated. If the collector area is increased well beyond the illuminated area in attaining PEF geometry, the fraction of electrons escaping the measurement will be reduced substantially. If the light is confined to a small, uniformly illuminated area and propagates through argon, the total number of UV photons striking the surface under inspection will become nearly independent of gap spacing. Absorption of the 184.9 nm line by oxygen would be eliminated. This would leave the major remaining factor of the inverse field relation to the spacing, but the variation of the field would be only in its strength and not in its shape. In these condiations, the OSEE current is not expected to increase a the inverse square root of the gap spacing, suggesting better data from the higher signal levels attained with smaller gap spacings. Countering these effects somewhat would be an increase in the capacitance between the collector electrode and the surface under inspection, which would lead to currents in responses to time variations of gap spacing, the process which drives capacitive microphones, if spacing is not carefully maintained.

Experiments have shown the OSEE currents to be sensitive to the contact potential between the instrument ground and the inspected surface, and the work function will vary with subtle changes in material properties of the surface independently of the presence of contaminants. The work function of a material is the amount of energy, usually measured in electron-volts, required to move an electron from the conducting, equipotential interior of a conductive material to the outside, theoretically to an infinite distance, but practically to any point removed from the immediate surface vicinity. It cannot be measured directly with an electrical measurement. If two dissimilar metals are connected with a conductive path, their outer faces differ in voltage by the difference of their work functions, a voltage called the contact potential. An electromechanical Kelvin probe is used to measure this contact potential which consists of a vibrating plate held close to the sampled surface with an adjustable bias voltage. When the bias voltage is set to a value such that the plate has no tendency to produce currents at the vibration frequency, the electric field between the plate and the inspected surface is zero, and the bias voltage is equal to the contact potential. A null-seeking circuit associated with such a device produces a measurement of the contact potential of the surface. With the contact potential measurement, the effect of contact potential changes on OSEE currents may be separated from that of contaminants.

If the contact potential between an electrode and a surface is measured by scanning the electrode over the surface and making a scan of such measurements, the spatial variations in measured contact potential are the same as the spatial variations in the work function of the surface.

The basic Kelvin probe consists of a vibrating plate positioned over the metallic surface being sampled, near 0.3 cm, but not touching. The change in voltage with the vibrating movement is monitored while the mean value of the voltage is changed. The mean value of applied voltage matches the contact potential of the underlying plate when the vibrating part of the voltage vanishes. For the realization of the Kelvin probe in the present work, a circuit was constructed which employed an electronic feedback loop to seek the null continuously, providing as output the voltage required to obtain the null.

Figure 11:
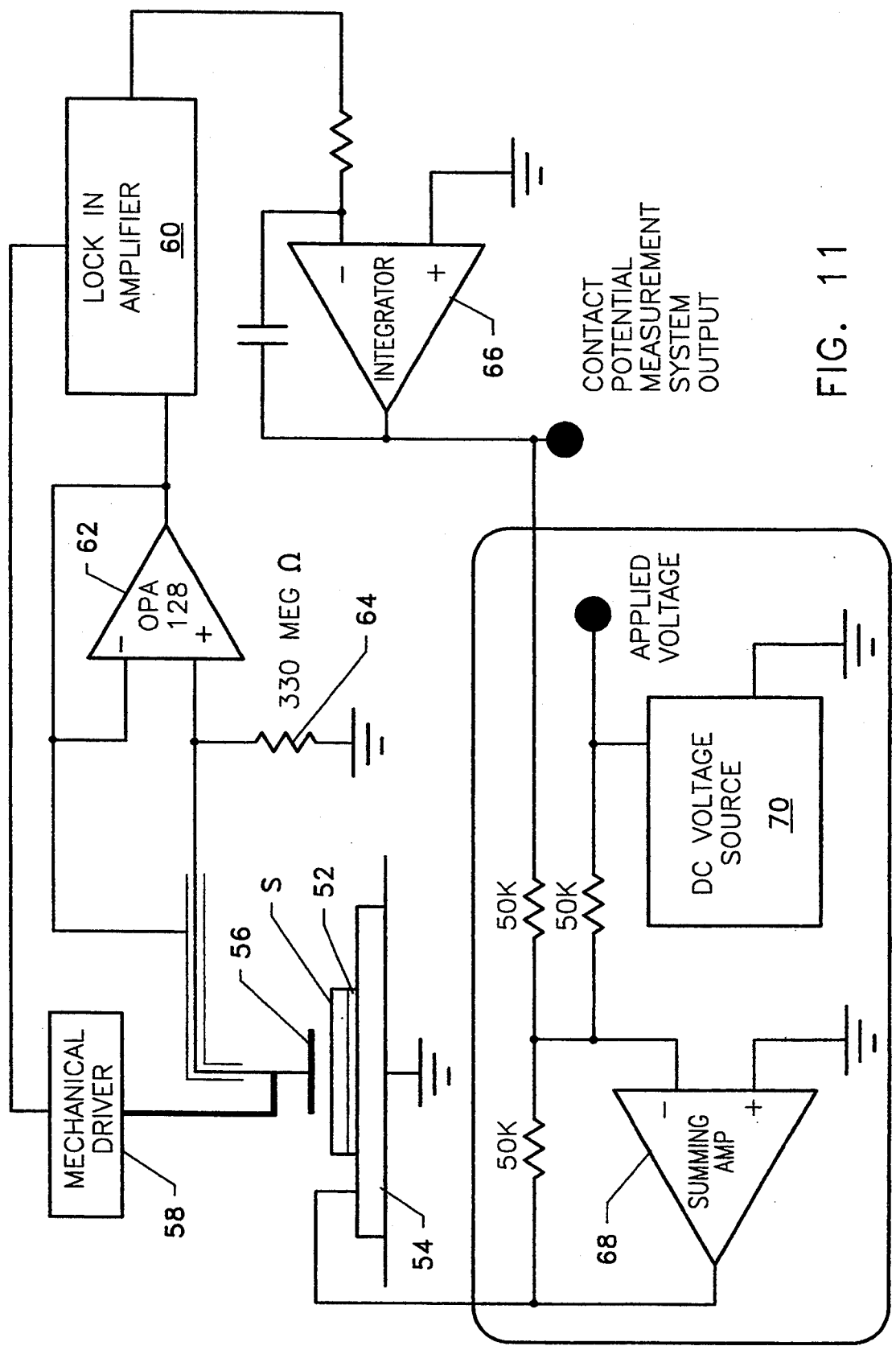
FIG. 11 is a schematic diagram of a Kelvin probe used in conjunction with the OSEE monitor according to the present invention.

FIG. 11 shows a schematic diagram of system operation. The sample is mounted on an insulator 52 over a ground plane 54, and a vibrating plate electrode 56 is placed over the sample facing the sample surface S and vibrated at constant amplitude by mechanical drive 58, the frequency and amplitude being set from the internal oscillator of a lock-in amplifier 60. An amplifier 62 such as an OPA128 operational amplifier available from Bun Brown has exceptionally high input impedance of better than $10^{14}\Omega$ with a bias current of only 75 fA, and it is operated as a unity gain amplifier and driver of the guard electrode. A 330 Megohm resistor 64 provides an effective path for any residual leakage through the OPA12S amplifier 62. The lock-in amplifier 60 detects the synchronous portion of the signal and provides the signal amplitude as input to an integrator 66. The output of the integrator 66 slews at a rate proportional to the signal amplitude voltage, the constant of proportionality being the inverse RC time constant of the external circuit components. The integrator output is inverted in a summing amplifier 68 and applied to a copper clad conducting surface attached to an insulator. The sample is placed on a copper surface, with test surface S directly below the vibrating plate. When the sum of the voltage applied to the surface under test and the contact potential between the test surface and the vibrating plate 56 is zero, the synchronous part of the signal vanishes, and the output of the integrator 66 remains at the contact potential between the plate 56 and the sample.

The summing amplifier 68 may be used in another manner, also, in that the voltage from an externally controlled source 70 may be added to the signal from the integrator. In this mode, the sum of the integrator voltage and the externally applied voltage must equal the integrator voltage with no applied voltage. The result is that the integrator finds equilibrium at an offset voltage, and the tracking ability of the integrator is tested. In a test of the system, the integrator tracked to within 0.5% of the applied voltage over a range from $-2$ V to 2 V, entirely adequate to measure contact potentials, which fall in the range of several tenths of a volt.

The Kelvin probe was used to measure contact potential differences in two situations. The significance of the measurement is that, while contact potential is associated with the difference in two work functions, the difference in contact potential under two sets of surface conditions is equal to the difference in the work function between the two conditions. The Kelvin probe was used to measure the contact potential variation between a clean sample and one contaminated with HD-2 grease. It was also used to measure the variability in work function among clean samples cut from the same sample of D6AC steel.

Figure 12A:
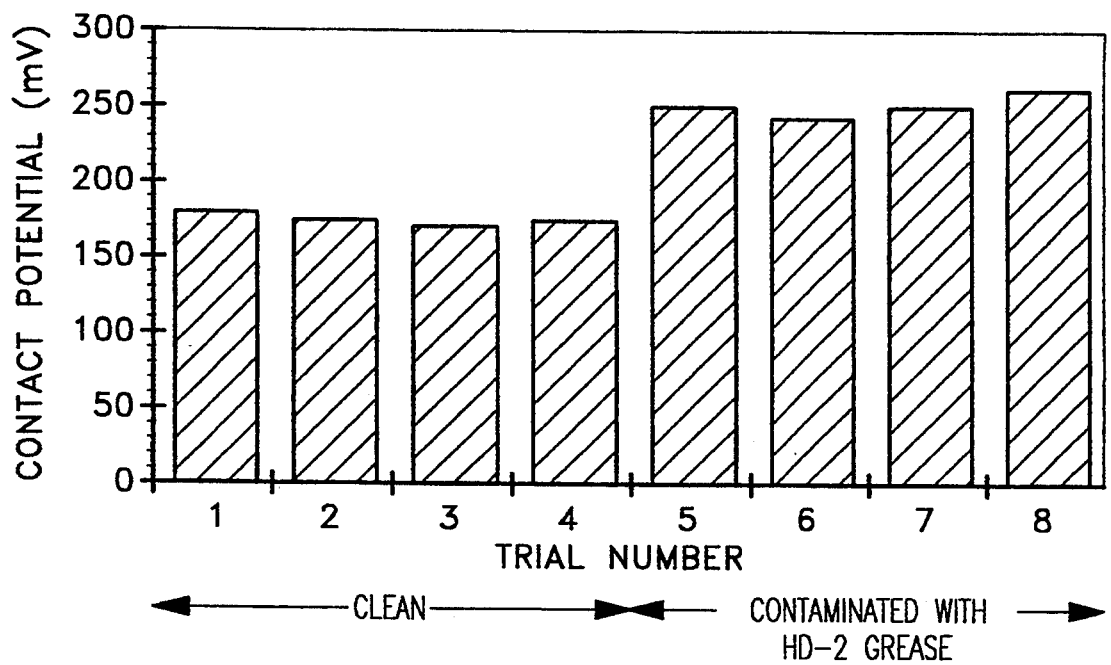
FIG. 12(a) is a graph of contact potentials for various samples measured with the Kelvin probe according to FIG. 11.

The first measurement is shown in FIG. 12(a). In this instance, two samples of D6AC steel were used. One was maintained in the clean condition and is shown as trials 1–4, and the other was contaminated with a large thickness of HD-2 grease and is shown as trials 5–8. Each sample was measured four times, with the sample removed from the apparatus and replaced for each measurement. The variability within each group of four readings is thus caused both by instrument variability and procedure variability, including the variability in position and contact as the sample was placed in the apparatus and the variability within each sample, as a slightly different area was sampled in the successive measurements. It is clear from FIG. 12(a) that all of the measurements on the clean sample are much different from those on the sample contaminated with grease, as the mean values are separated by about 90 mV, while the deviations from the mean are all less than 6 mV. It is also noted that the deviations from the mean for the contaminated sample are not significantly different from those of the clean sample. No great care was taken to control the thickness of the contaminant in this experiment. The lack of increase of the variations around the mean suggests that the change in work function is associated with the presence of grease rather than the thickness of the grease layer, at least for thick layers above several nanometers. Also noted is that the deviation shows no strong trend as a function of trial number, the trials being numbered consecutively as they were performed. This indicates that long term drift mechanisms were not the largest contributors to the observed variability over the duration of the test.

Figure 12B:
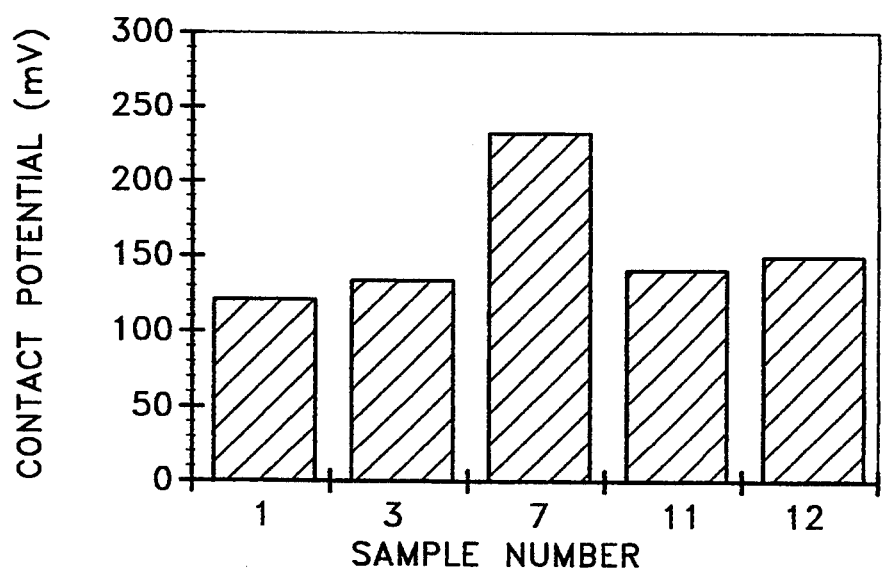
FIG. 12(b) is a graph of contact potential for selected samples measured with the Kelvin probe according to FIG. 11.

The second measurement with the Kelvin probe, shown in FIG. 12(b), was used to examine a possible cause for the observed variability in OSEE readings for the various clean samples. It was found during the OSEE tests for contamination that a particular sample, number 7, consistently had small values for OSEE currents. The small values persisted even when the sample was repeatedly cleaned and, finally, sandblasted for a second time. If the diminished values of OSEE current were not attributable to contamination, they were possibly associated with some property of the substrate which would change the work function. In an effort to examine this possibility, contact potential measurements were obtained for various clean samples, and sample 7 did exhibit an unusually high value of contact potential. A high contact potential for a surface is consistent with a low OSEE current. Thus, the data from the anomalous sample are consistent with the hypothesis that work function variability in the underlying D6AC steel causes a significant portion of the variation in OSEE currents even in uncontaminated samples.

Examining the variability of the Kelvin probe readings for all of the measurements by groups, the estimates of the standard deviations are 4.2 mV for the contaminated sample, 3.9 mV for the uncontaminated sample and 14.6 mV for the four samples remaining when the anomalous one is removed from consideration. The inter-sample variability of contact potential for clean samples cut from a single square foot of D6AC steel is thus substantially greater than the variability which can be attributed to instrument noise and measurement protocol. Because the anomalous sample was removed from the set of samples obtained from that single plate, this variability estimate may be considered the minimum estimate one might make of spatial variability of contact potential in D6AC steel. The difference between the value for the sample used for the clean measurement of the contamination study and the average of the "non-anomalous" samples from the single plate is 38 mV, which amounts to 2.6 standard deviation estimates. In this context, that is not enough to establish statistical separation, because the origin of the clean member of the contamination sample pair probably came from another plate of steel, perhaps even from another process batch. If that value is considered part of the "clean steel" set, the average contact potential for clean samples increases by only 7 mV, while the standard deviation increases by about half to 21.3 mV. The anomalous value is still separated from this mean by 4.5 standard deviation estimates. With either interpretation, the value for the anomalous sample remains statistically far from the mean and close to the value for contaminated samples. The strongest evidence for the anomaly of the anomalous sample not being due to contamination remains that its OSEE representation persisted in a stable manner through several cleanings and resandblasting of the surface.

In summary, an instrument was developed to measure contact potential of D6AC steel sample. With the instrument, the contact potential of a surface contaminated with HD-2 grease was shown to be significantly higher than that of an uncontaminated sample. In addition, D6AC steel was shown to have a large variability of contact potential over its surface. The variability of contact potential was shown to correspond with observed variability of OSEE currents in clean samples. These findings have several implications for surface inspections. First, they identify a non-contaminant cause for OSEE reading variations. Second, they suggest that contact potential measurements may provide another mode for inspection of surfaces for inspection. This mode would, of course, be subject to the same variability as OSEE is. Finally, the findings suggest that a dual measurement using both OSEE and Kelvin probe measurements should be used to remove the variability due to substrate contact potential variability from the contamination measurement.

The prototype Kelvin probe contact potential instrument demonstrated that such a probe can be realized outside of a vacuum environment and does provide measurements of relevance to the OSEE inspection environment. The improvements listed below are those with potential for realization with a Kelvin probe used in conjunction with the OSEE measurement.

In an OSEE measurement, the reduction of photocurrent observed on a contaminated surface compared to a clean surface is due to two effects; namely, (1) change in surface work function and (2) absorption of incident light. The Kelvin probe measurement is sensitive to only the first of these effects. Further, for a given substrate, the change in work function is a property of the contaminant, and so its measurement may be used to discriminate among contaminants.

With the separate measurement of contact potential variation, and hence work function change, the two factors in OSEE photocurrent may be separated out. By adjusting for the contact potential change with a voltage-current characteristic curve for the gas in the OSEE cell, the current reduction solely due to contaminant absorption is obtained. If the contaminant and its absorption rates are known for the various wavelengths of the incident light, the thickness of the contaminant may be determined. The net result is that, in circumstances producing relatively pure contamination spots from a variety of contaminant species, the species may be discriminated with the Kelvin probe part of the measurement, and then the thickness of the contaminant may be determined with the OSEE reading.

In any measurement, the "point" inspected consists of a finite area over which the measurement physics are actually operating. This may be thought of as the "footprint" or zone of influence of the measurement. The measurement actually consists of some weighted average of the property measured over the zone of influence. With many measurements, the averaging function remains constant over a series of measurements. Because of the strong dependence on work function and the exponential dependence of light absorption on contaminant thickness, the OSEE measurement weighting function can vary from measurement to measurement. This variation adds a complicating factor to interpretation of the measurement. The Kelvin probe measurement performs an average over the moving element, if it is held flat over the sample surface. Thus, its weighting function is particularly simple in form and remains constant from measurement to measurement.

When OSEE probes are brought close to non-conducting substrates, they show current arising from electron emission from the substrate. It is reasonable to suppose that these currents are associated with electrons released from the material. Unlike metals, however, the removed electrons cannot be replaced from a conductive pool. The currents decrease and eventually cease as the available electrons are removed. The effect may be seen as a positive charging of the surface under OSEE examination. The initial current for the sample is a function of, among other things, its initial charge value. This can be altered by many factors, including handling prior to inspection. In order to obtain an OSEE reading which depends primarily on surface contamination, it would be necessary first to establish a standard state of charge. Such a state could be established by incorporating a Kelvin probe in the measurement and obtaining the OSEE reading when the Kelvin probe indicated some standard voltage.

There is sometimes interest expressed in applying the OSEE technique to non-metallic surfaces. For these surfaces, the application of the OSEE technique alone will probably produce confusing results, but there is some potential that a hybrid OSEE/Kelvin probe might obtain some useful information. The kinds of materials which might be encountered are, for the purpose of considering the OSEE response and possible inspection protocols, divided into nonconductors, semiconductors and photoconductors.

For some nonconductors, there is no OSEE current generated. For these, OSEE inspection is, in general, unsuitable. A possible exception to this is that some photocurrent might be obtained if the contaminant is a photoemitter under OSEE inspection. On the other hand, the Kelvin probe can be used to examine the charge profile of the surface. For other nonconductors, transient OSEE currents are obtained. There is some potential that a combination use of OSEE and Kelvin probe techniques can provide standard surface charging conditions and produce values which contain information primarily about contamination.

For semiconductors, the inspection lamp promotes electrons from the valence band to the conduction band. These electrons may be released under further illumination, providing OSEE signals. If the materials had high purity as those used for electronic purposes do, the electrons can also travel for macroscopic distances through the material before being absorbed back into the valance band. As a result, semiconductor surfaces would appear similar to metallic surfaces, for the electrons within the material would be mobile. Thus, OSEE alone may be of value inspecting semiconductor surfaces of electronic grade purity.

In photoconductors, electrons are mobile while directly under the illumination of the OSEE lamp. These will produce pools of conductivity to the depth that the incident radiation penetrates. These electrons can be released under OSEE inspection, and stable currents are obtainable over short periods of time. The released electrons, however, exist only in a region directly under the illumination, and as they are removed, surface charging can occur with a coincident loss of photocurrent. In this case, the concurrent measurement with the Kelvin probe will be beneficial to monitor the surface voltage. One interesting possibility is that a combination OSEE/Kelvin probe could be used to distinguish between semiconductors and photoconductors in a non-contacting manner, the illumination based on the amount of charging for a given illumination.

In the conventional OSEE monitor of FIG. 1, the bias voltage on the collector is produced by a battery built into the probe. This puts a practical ceiling on the voltage which can be attained and precludes changing the voltage during a measurement cycle. The improvement here is to provide the voltage from a source external to the head which can be controlled during a measurement. This control permits more flexibility and variety in the measurement protocols which can be embodied in an OSEE measurement.

More specifically, in the commercial unit the voltage source for the bias voltage is a battery 16 located within the probe head, as shown in FIGS. 1 and 13(a). The bias battery 16 is located in the circuit between the collection grid 18 and the first amplification stage 20, which is operated near ground potential. While this scheme has some definite advantages, it does not facilitate varying the bias voltage. By externally controlling the voltage source, in one embodiment by simply supplying the voltage externally, control is gained over an important variable in the measurement. In the embodiment shown in FIG. 13(a) the voltage source is controlled by supplying an external voltage which biases the sample, so that the collector electronics can operate near ground potential. In a unit for inspection of large objects maintained at ground potential as shown in FIG. 13(b), the signal preamplifier is operated at a high potential and the amplifier signal is brought to near ground potential with an isolation amplifier. In both FIGS. 13(b) and 13(c), the paired arrows represent connections to external bias supply 21 as shown in FIG. 13(c). The ability to vary only the bias voltage in an OSEE measurement system has permitted the experimental determination of the voltage-current characteristic of an OSEE cell and has enabled the current reversal used to achieve charge replacement on measurements of insulating surfaces as discussed above.

Standard OSEE measurements produce non-reproducible values on insulating surfaces because there is no mechanism for replacing electrons which have been released by the light. One result of this is that the charge state of the surface is poorly defined during a sequence of repeated measurements, resulting in non-repeating OSEE measurements. One way to improve the repeatability is to reverse the bias of the measurement until an amount of charge has been transferred in the reverse direction equal to the charge transferred during the measurement. This technique is called charge replacement. Another possible way is to "bathe" the area under inspection in an ion field prior to measurement.

With conductors, photoelectric-induced emission, i.e., photoemission, of electrons occurs as photons of sufficient energy are absorbed by electrons in the metal which are located in the so-called band of conduction electrons. Some of these "energized" electrons escape free of the metal by overcoming a potential barrier called the work function. This leaves a vacancy in the conduction band. Because the metal is part of a closed loop, each electron vacancy in the metal is filled with a replacement electron from another location in the loop.

With insulators, photoemission removes statically located charges in the form of electrons or negative ions, leaving a net charge at the sites. Because there is no appropriate band, i.e., no appropriate quantum-mechanical conditions for conduction in the material, by which charges can migrate, the statically located charge sites remain charged. This means that eventually all charges capable of being removed by the electromagnetic radiation will have been removed. The formal description of the total process is given by $$\frac{dq}{dt} = -Kq \qquad (1)$$

where q is the charge on the insulator that can respond to the electromagnetic radiation. For a given set of conditions K is a constant that to first order depends upon the surface density of "available" negative surface charges, their unbinding energy, the intensity of the radiation, and the probability of interaction of the radiation with the available negative surface charges. The adjective "available" means the negative charge associated with the electrons that can interact with the radiation. Many surface electrons or negative ions are too tightly bound to the material to be removed by the electromagnetic radiation and are hence "unavailable ". The minus sign in Eq. (1) indicates that the action depletes the number of available negative surface charges. It should be pointed out that as a contamination thickness increases, K changes.

The integration of Eq. (1) with appropriate limits of integration gives that $$q = q_0 e^{-Kt} \qquad (2)$$

where t is time and $q_0$ is the amount of available charge on the conducting surface. Differentiating Eq. (2) gives i, the OSEE current, dq/dt, as a function of time as $$i = K\, q_0 e^{-Kt}. \qquad (3)$$

This predicts that as the surface of the insulator is bombarded with sufficiently high frequency electromagnetic radiation, negative surface charges will be liberated but the number of available negative surface charges on the insulator surface will consequently decrease.

In order to engage in reproducible measurements on insulators, one must assure that whenever measurements are made, one knows that the number of available surface charges, $q_0$, is the same. To ensure that this condition is met the previously removed charges should be replaced. One way for replenishment is to operate the OSEE probe in reverse conditions so that charges can be forced back onto the insulator, i.e., to reverse the bias of the collector. Another way is the passage of the insulator through an ion field. The ion field provides a source of both positive and negative charges so that the opposite charge in the ion field can migrate and attach to the statically located charge sites on the insulator, thus replenishing the supply of available surface charges on the insulator that can participate in photoemission. Any other process which resupplies the available charge onto an insulator are appropriate.

Once the available charges have been replenished, the measurement process can occur. Because the contaminat absorbs some of the electromagnetic radiation before it reaches the surface of the insulator, fewer electrons are released directly beneath the contaminant. Thus, a decrease in the initial OSEE current occurs, as the OSEE current obeys Eq. (1).

$$i = \frac{dq}{dt} = -K'q_0 \tag{4}$$

where K' is the new constant of proportionality. K' depends upon the intensity of the electromagnetic radiation that reaches the insulator surface and hence on the contaminant absorption and the thickness. Therefore, the amount of the electromagnetic absorption of the contaminant directly affects the OSEE measurement of a charge-replenished insulator surface.

Consider an insulator or non-metal which is to be tested for contamination. The first step is to bombard the surface with high intensity ultraviolet radiation in the presence of an electric field to remove a large number of the available negative surface charges on the insulator surface. The next step is to immediately expose the insulator to an ion field sufficiently long that the surface no longer exhibits a net charge state. Now the insulator is ready for the OSEE-based measurement technique described above.

Many improvements, modifications and substitutions will be apparent to the skilled artisan without departing from the spirit and scope of the present invention as defined herein and desirable in the following claims.

We claim:

1. An apparatus for performing quality inspections on a test surface based on optically stimulated emission of electrons comprising:
   (a) a light source for directing ultraviolet light onto the test surface;
   (b) means for detecting a current of photoelectrons emitted from the test surface and generating a signal indicative of the photoelectron current, said means for detecting including a collector for collecting the photoelectron current and means for positively biasing said collector with respect to the test surface;
   (c) means for indicating a condition of quality based on the generated signal indicative of photoelectron current; and
   (d) means for negatively biasing said collector with respect to the test surface to replace charges removed as photoelectron current from the test surface by the previously positively biased collector.

2. The apparatus according to claim 1, wherein said light source directs a spectrum comprising discrete lines of ultraviolet light onto the test surface, the lines of the spectrum releasing photoelectrons from the test surface, and further comprising a light filter located between said light source and the test surface for permitting a selected spectrum line to pass through and for filtering out any other spectrum lines, wherein the selected spectrum line produces a majority of the photoelectron current produced by the spectrum.

3. The apparatus according to claim 1, further comprising means for supplying the test surface with a purge gas which is transparent to the ultraviolet light, does not alter the test surface, and does not participate in photochemistry.

4. The apparatus according to claim 1, further comprising an airtight enclosure surrounding the test surface, said light source and said detecting means; means for supplying the airtight enclosure with a purge gas; and means for circulating the purge gas through said airtight enclosure.

5. The apparatus according to claim 1, wherein said collector comprises a wire grid located between said light source and the test surface, said wire grid defining apertures for the ultraviolet light to pass therethrough, said wire grid oriented to form parallel electric field lines and constant potential surfaces.

6. The apparatus according to claim 1, further comprising means for determining a contact potential of the test surface.

7. The apparatus according to claim 6, wherein said contact potential determining means is a Kelvin probe.

8. The apparatus according to claim 1, further comprising:
   a voltage source for powering said light source;
   a detector for detecting the intensity of a particular wavelength of light directed by said light source onto the test surface and producing a signal indicative of the detected intensity; and
   means for controlling the voltage of said voltage source in response to the signal indicative of the intensity of the particular wavelength to maintain the signal at a constant value indicative of a desired intensity of the particular wavelength of light.

9. The apparatus according to claim 1, further comprising:
   an airtight housing located around said light source, said housing having a window which is transparent to the ultraviolet light of said light source; and
   a gas circulation system for circulating a cooling gas through said housing to cool said light source, the cooling gas being transparent to the ultraviolet light of said light source.

10. The apparatus according to claim 8, further comprising:
    an airtight housing located around said light source, said housing having a window which is transparent to the ultraviolet light of said light source; and
    a gas circulation system for circulating a cooling gas through said housing to cool said light source, the cooling gas being transparent to the ultraviolet light of said light source.

11. An apparatus for performing quality inspections on a test surface based on optically stimulated emission of electrons comprising:
    (a) a light source for producing and directing ultraviolet light onto the test surface;
    (b) means for detecting a current of photoelectrons emitted from the test surface and generating a signal indicative of the photoelectron current, said means for detecting including a collector for collecting the photoelectron current and means for positively biasing said collector with respect to the test surface, wherein the collector comprises a window transparent to the ultraviolet light directed by said light source, a metal layer coated on the window which is partially transparent to the ultraviolet light directed by said light source; and
    (c) means for indicating a condition of quality based on the generated signal indicative of photoelectron current.

12. A method of performing quality inspection on a test surface based on optically stimulated emission of electrons comprising the steps of:
    directing ultraviolet light on the test surface;
    positively biasing a collector with respect to the test surface to collect the photoelectrons emitted from the test surface, whereby a certain charge is removed from the test surface;
    measuring the current of photoelectrons emitted from the test surface;

correlating the measured photoelectron current with a condition of quality; and negatively biasing the collector with respect to the test surface until an amount of charge equal to the certain amount of charge transferred during the measurement step is replaced to the test surface.

13. A method of performing quality inspection on an insulator test surface comprising the sequential steps of:

bombarding the insulator test surface with ultraviolet radiation in the presence of an electric field to remove negative charges from the insulator test surface;

exposing the insulator test surface to an ion field until the insulator test surface no longer exhibits a net charge status;

directing ultraviolet light on the test surfaces;

measuring a current of photoelectrons emitted from the test surface; and correlating the measured photoelectron current with a condition of quality.

* * * * *